United States Patent
Kaiser et al.

(10) Patent No.: US 7,697,985 B2
(45) Date of Patent: Apr. 13, 2010

(54) SYSTEM AND METHOD FOR PROVIDING ALTERNATIVE PACING MODALITY SELECTION

(75) Inventors: Daniel R. Kaiser, St. Paul, MN (US); John E. Burnes, Andover, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 263 days.

(21) Appl. No.: 11/189,488

(22) Filed: Jul. 26, 2005

(65) Prior Publication Data

US 2007/0027488 A1    Feb. 1, 2007

(51) Int. Cl.
*A61N 1/362* (2006.01)

(52) U.S. Cl. ............................................. 607/9; 607/27
(58) Field of Classification Search ..................... 607/9, 607/27, 28, 52
See application file for complete search history.

(56) References Cited

U.S. PATENT DOCUMENTS

| | | | |
|---|---|---|---|
| 4,428,378 A | 1/1984 | Anderson et al. | |
| 5,052,388 A | 10/1991 | Sivula et al. | |
| 5,549,646 A * | 8/1996 | Katz et al. | 607/8 |
| 5,814,088 A * | 9/1998 | Paul et al. | 607/28 |
| 6,721,600 B2 * | 4/2004 | Jorgenson et al. | 607/27 |
| 6,772,005 B2 * | 8/2004 | Casavant et al. | 607/4 |
| 6,871,096 B2 | 3/2005 | Hill | |
| 7,283,872 B2 * | 10/2007 | Boute et al. | 607/8 |
| 2004/0260349 A1 | 12/2004 | Stroebel | |
| 2005/0256547 A1 * | 11/2005 | Stahmann et al. | 607/27 |

FOREIGN PATENT DOCUMENTS

| | | |
|---|---|---|
| EP | 0338363 A2 | 10/1989 |
| WO | WO0218010 A2 | 3/2002 |
| WO | WO03037427 A1 | 5/2003 |
| WO | WO2004026397 A1 | 4/2004 |

* cited by examiner

*Primary Examiner*—Carl H Layno
*Assistant Examiner*—Brian T Gedeon
(74) *Attorney, Agent, or Firm*—Stephen W. Bauer

(57) ABSTRACT

An implantable medical device (IMD) identifies lead performance issues and provides alternative lead configurations to continue with the programmed therapy. In the absence of an appropriate alternatively lead configuration, the IMD determines alternative mechanisms to provide a similar therapy or to determine a secondary therapy.

19 Claims, 10 Drawing Sheets

SYSTEM AND METHOD FOR PROVIDING ALTERNATIVE PACING MODALITY SELECTION

FIELD OF THE INVENTION

The present invention relates to medical devices and more specifically to medical devices having multiple pacing modalities.

DESCRIPTION OF THE RELATED ART

Various implantable medical devices (IMD) have been provided that include a variety of physical configurations and pacing modes that facilitate different therapies. For example, a given patient may have complete conduction block and require permanent ventricular pacing (pacemaker dependant). In that context a V (ventricular) pace is always delivered after a given trigger, such as an intrinsic atrial depolarization or an atrial pacing pulse.

In other contexts, the patient may retain some degree of intrinsic conduction. Whenever possible it is preferable to rely on the patient's own conduction rather than providing a ventricular pacing stimulus. In order to promote such intrinsic connection, Medtronic, Inc. has developed new pacing protocols referred to herein as Ventricular Pacing Protocols (VPP). Managed Ventricular Pacing™ (MVP™) is a commercial embodiment of one VPP. Various embodiments of VPPs described in application Ser. No. 10/755,454, filed Jan. 12, 2004, which is a continuation of U.S. Publication No. 2003/0078627 A1, published Apr. 24, 2003, which is a continuation-in-part of application Ser. No. 09/746,571, filed Dec. 21, 2000, now U.S. Pat. No. 6,772,005, and in U.S. Publication No. 2004/0260349 A1, published Dec. 23, 2004, all of which are herein incorporated by reference in their entirety. As a high level summary and to facilitate a general understanding (which is in no way meant to be complete or limiting to the above-referenced patents and applications) a VPP is a protocol that operates in a manner similar to an atrial based pacing mode such as AAI/R, but with ventricular sensing. A full cardiac cycle without a ventricular event is tolerated, with a ventricular pace provided in the subsequent cycle. The protocol returns to the atrial based mode until a predetermined number of ventricular beats (out of a certain number of cycles) are missed. Then the protocol operates in a dual chamber mode (e.g., DDI/R or DDD/R) with intermittent conduction checks to determine if conduction has returned. In this manner, intrinsic conduction is promoted and ventricular pacing is reduced or minimized. This is particularly beneficial when a ventricular pacing lead is placed in the right ventricular apex. The VPP may effectuate the result through various mode switches (and thus is a protocol using multiple modes) or by operation in a single mode having operable characteristics of multiple modes; thus avoiding or reducing the necessity for mode switching for each type of action.

Another beneficial pacing protocol is cardiac resynchronization therapy (CRT). In summary, certain patients (particularly those suffering from congestive heart failure) have generally intact intrinsic atrial-ventricular conduction; however, their ventricular timing is unsynchronized. Thus, ventricular depolarization becomes inefficient and cardiac output is reduced. This often leads to a further decline in the patient's health and heart failure status.

Bi-ventricular pacing is a form of CRT and provides ventricular pacing in both ventricles; that is, a pacing lead is placed within the right ventricle and a second lead is typically placed in a cardiac vein over the left ventricle or an epicardial lead is affixed. Thus, timing is controlled from the atrium to the right ventricle (A-RV) as well as from the atrium to the left ventricle (A-LV). As these parameters can be set independently, V-V timing can be set accordingly, resulting in a resynchronized contraction with an improved cardiac output. In heart failure patients, "remodeling" of the heart may occur as a result, which improves the patient's overall condition.

Fusion pacing is another form of CRT and achieves an effect similar to bi-ventricular pacing, yet only requires left sided ventricular pacing. In patients with heart failure, intrinsic conduction from the AV node through the right ventricle may be relatively normal as compared to conduction from the AV node and through the left ventricle. Thus, a pacing stimulus is delivered to the left side and is correlated to the intrinsic conduction in the right ventricle. That is, the intrinsic RV activation time is determined using previous beats and an LV pace is delivered prior to a corresponding RV event so that the resultant ventricular depolarization and contraction in both ventricles is more hemodynamically efficacious. Thus, the ventricles are again re-synchronized and only left sided pacing is required. Fusion pacing is typically performed based upon timing generated by sensed events in the right ventricle; thus, while right side ventricular pacing is not required, sensing capabilities are utilized. This may include the placement of a lead into the right ventricle, though other sensing mechanisms are also available. The following patents and applications are relevant and are incorporated herein by reference in their entireties; U.S. Pat. No. 6,871,096, filed Oct. 26, 2001 and U.S. Ser. No. 10/803,570, filed Mar. 17, 2004.

Based on the present discussion, ventricular pacing is separable into two broad, overlapping classifications. The first is to synchronize contraction and improve the performance of the ventricles and underlying intrinsic conduction may or may not be present. The second is to initiate ventricular depolarization either in the absence or presumed absence of intrinsic conduction. Thus, with complete heart block, the patient is pacemaker dependant and will always require ventricular pacing. With lesser degrees of conduction block, intrinsic conduction may or may not be present for any given cycle. Within this second category, VPPs such as MVP™ are useful to promote intrinsic conduction and reduce unnecessary pacing. It should be appreciated that various tachyarrhythmias may result in the delivery of various pacing therapies (e.g., anti-tachy pacing) that are distinct from the present discussion.

Another mechanism for addressing the second category and to avoid the effects of single chamber ventricular pacing at the right ventricular apex is to place a lead at the Bundle of His or subsequent location along the intrinsic conduction system such as the RBB or LBB. After an appropriate AV delay, a pacing stimulus delivered to the electrode on the intrinsic conduction system effectuates ventricular depolarization in much the same manner as intrinsic conduction. Of course, any abnormalities in the conduction pathway subsequent to the pacing site may still interfere with depolarization.

The nature of the patient's condition and the expected development over time will direct the implanting physician or caregiver as to which device configuration to implant and which protocols to employ

DETAILED DESCRIPTION

Figure 1:
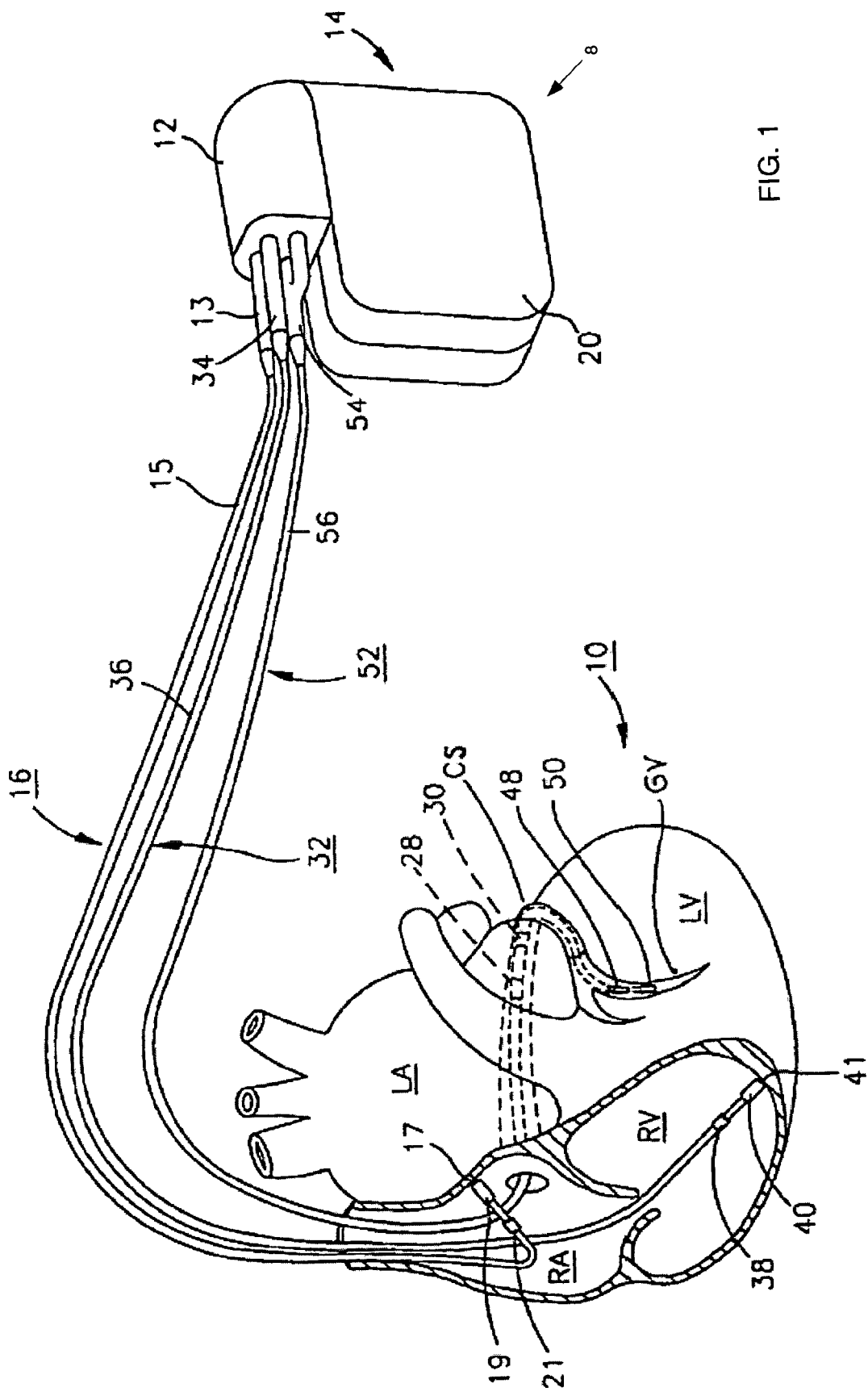
FIG. 1 is an isometric, partially sectional schematic illustration of an exemplary implantable medical device (IMD) having leads positioned within three chambers of a heart.

FIG. 1 is a schematic representation of an implantable, triple chamber cardiac pacemaker (IPG) 14 and associated leads 16, 32. Such a device is merely exemplary of an embodiment of the types of devices useful with the present invention. In general, such devices are collectively referred to as implantable medical devices (IMD) 8 and include pacemakers, cardioverters, defibrillators and any combination thereof. The IPG 14 is typically implanted subcutaneously in a patient's body between the skin and the ribs. Three leads 16, 32, 52 connect the IPG 14 with the right atrium RA, the right ventricle RV and the left ventricle LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals, e.g. a far field R-wave (FFRS). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. Additional embodiments include entirely subcutaneous devices that do not utilize leads positioned within the vasculature or interior of the heart 10; rather electrodes are positioned external to the heart in appropriate locations.

The depicted bipolar endocardial RA lead 16 is passed through a vein into the RA chamber of the heart 10, and the distal end of the RA lead 16 is in contact with the RA wall utilizing an active or passive attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, coronary sinus (CS) lead 52 is passed through a vein and the RA chamber of the heart 10, into the coronary sinus and then inferiorly in a branching vessel to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein. Alternatively, a bipolar or unipolar epicardial lead may be attached to the heart without the use of a coronary sinus vein to obtain adequate LV pace/sense function. Alternatively, a bipolar or unipolar lead may be placed in the LV endocardium from transmural access.

In a four chamber or channel embodiment, LV CS lead 52 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 2:
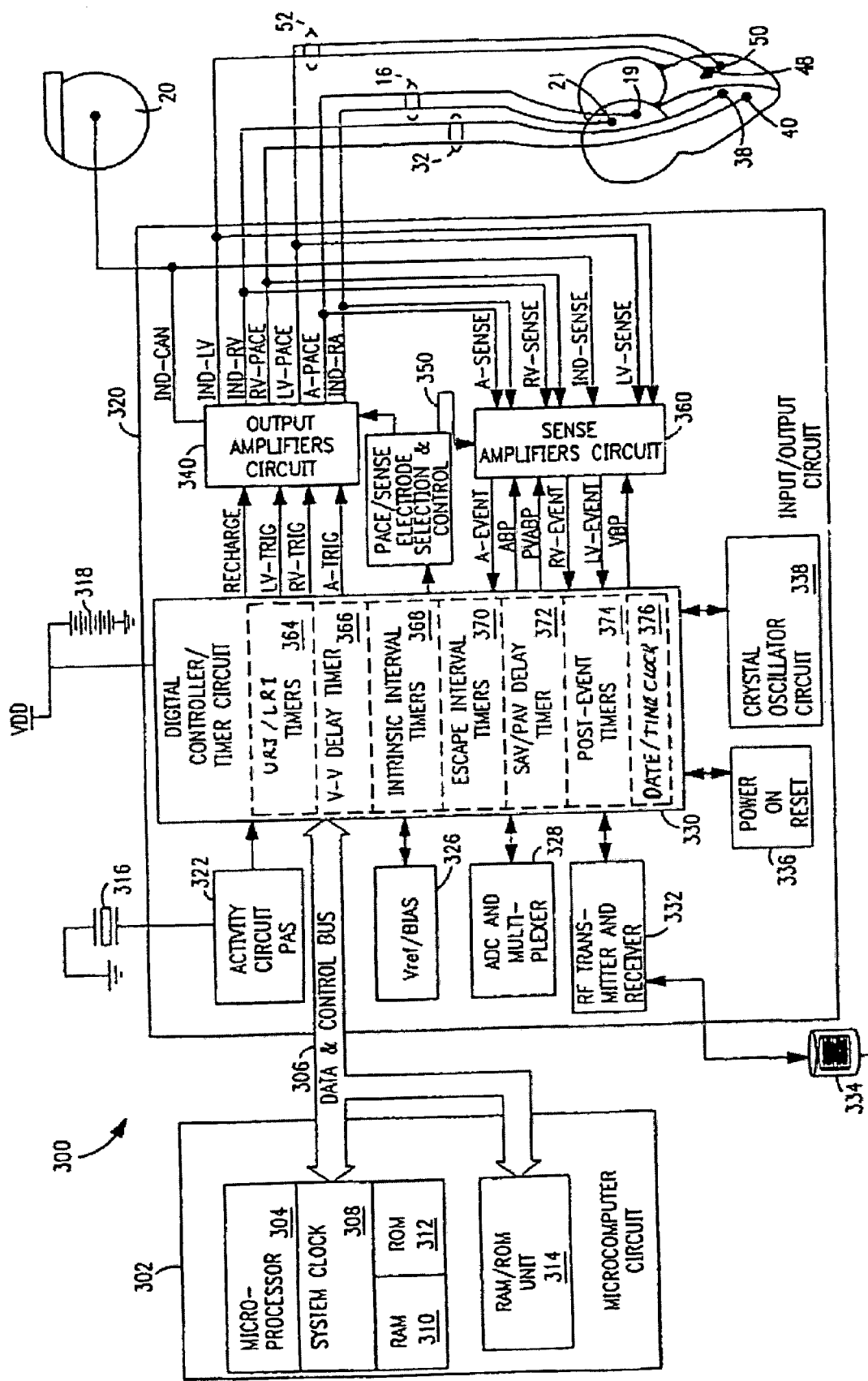
FIG. 2 is a block diagram illustrating the components of the IMD of FIG. 1.

In this regard, FIG. 2 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A. V-A or V-V escape interval. In addition, the microprocessor 304 may also serve to define variable AV delays and the bi-ventricular V-V pace delays from the activity sensor data.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing the A-LVp delay and A-RVp delay from a preceding A-EVENT or A-TRIG, a post-ventricular timer 374 for timing post-ventricular time periods, and a date/time clock 376.

Figure 7:
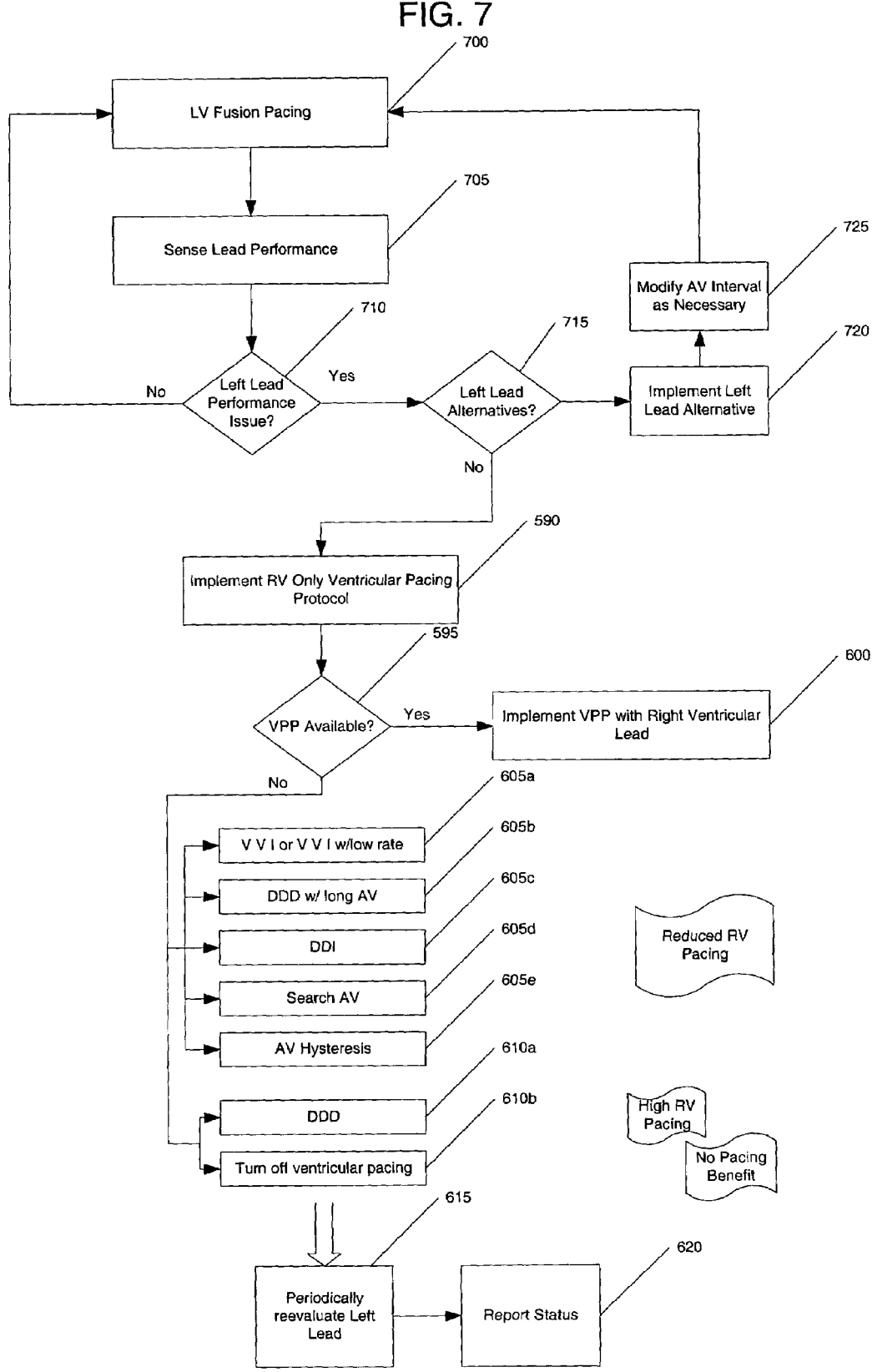
FIG. 7 is a flowchart illustrating a process for addressing left side lead performance issues during Fusion pacing.

In one embodiment, the AV delay interval timer 372 is loaded with an appropriate A-RVp delay and an A-LVp delay as determined in FIG. 7 to time-out starting from a preceding A-PACE or A-EVENT. It should be noted that the V-V delay timer 366 could be employed to time out an equivalent V-V delay that represents the difference between the A-RVP delay and the A-LVp delay. In that case, the difference between the A-RVp delay and the longer A-LVp delay would be determined. The interval timer 372 would time out the A-RVp delay, but typically not generate the RV-TRIG because of an RV-EVENT interrupting the timing, and then the V-V delay timer 366 would time out the difference and generate the LV-TRIG signal.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled.

It should be noted that the starting of the post-atrial time periods and the AV delays can be commenced substantially simultaneously with the start or end of the A-EVENT or the A-TRIG or, in the latter case, upon the start of end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the start of end of the V-PACE which may follow the V-TRIG.

The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay and the LV-TRIG at the time-out of the A-LVp delay provided by AV delay interval timer 372 (or the V-V delay timer 366). Similarly, digital controller/timer circuit 330 generates an RA-TRIG signal that triggers output of an RA-PACE pulse (or an LA-TRIG signal that triggers output of an LA-PACE pulse if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The above described IMD 8 is exemplary of a device that may include single, dual, triple or even four chamber pacing along with defibrillation and cardioversion capabilities. Though not separately illustrated, electrode 40 and attachment mechanism 41 (or a similar or duplicative lead) may be positioned in proximity to the Bundle of His along (or into) the inter-ventricular septum.

Figure 3:
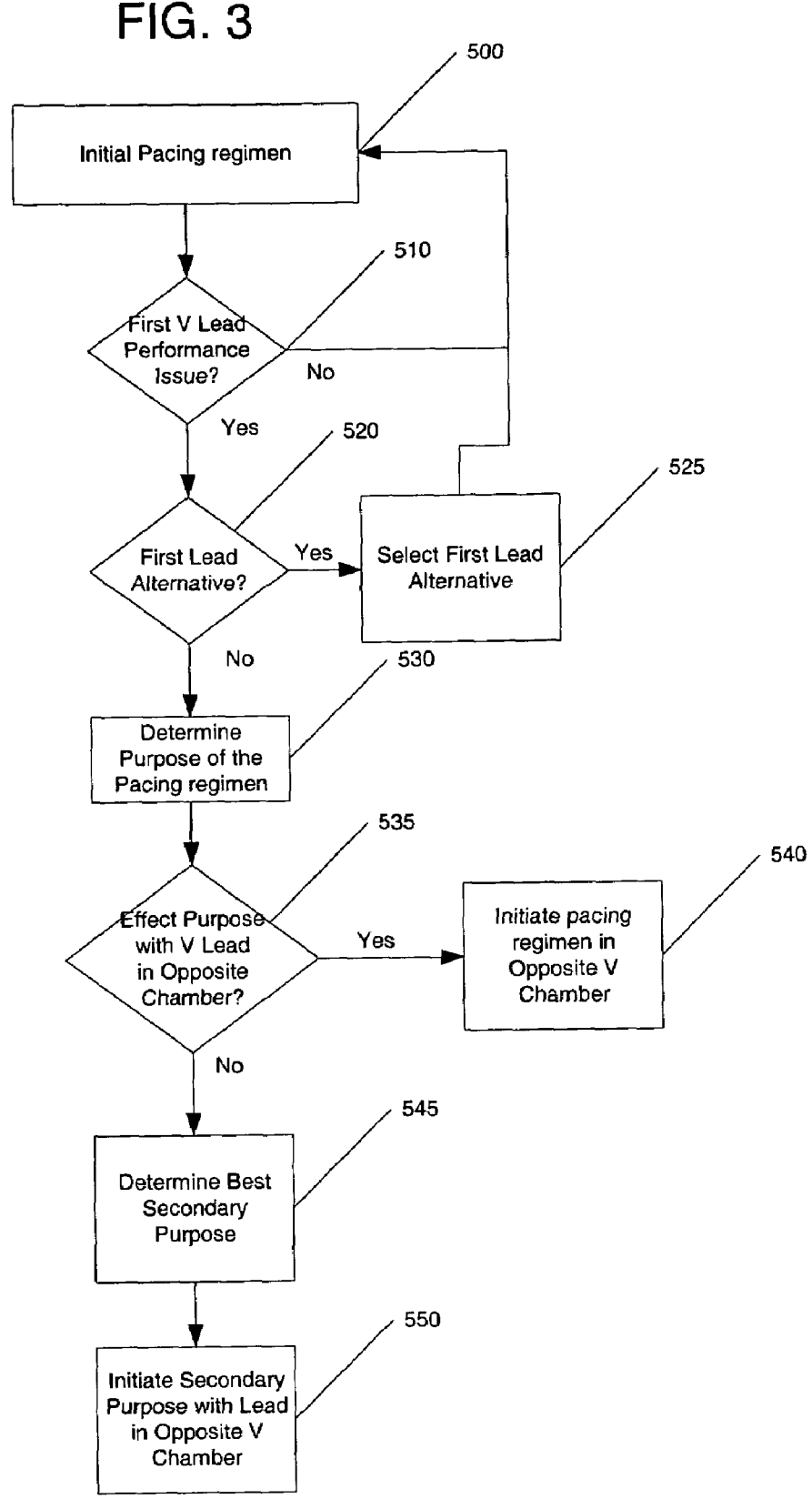
FIG. 3 is a flowchart illustrating a process for identifying and addressing a lead performance issue.

Referring to FIG. 3, an overview of a process according to the present invention is illustrated. Initially a patient will come to a physician and the physician will prescribe the implantation of a given device. Then depending upon the particular condition, the physician will configure the device to provide a particular pacing regimen. For example a patient suffering from heart failure may have an IMD configured to provide cardiac resynchronization therapy (CRT). In this example, CRT becomes the initial pacing regimen 500. As will be described in greater detail below various other pacing regimens will take on the status of the initial regimen 500 in different circumstances.

Regardless of which pacing regimen is initially in place, one or more leads each having one or more electrodes is utilized. Depending upon the therapy, a given lead may be more critical for a particular task or each may have similar importance. For example, in Fusion pacing, the left side lead typically is critical for delivery of the pacing stimulus, whereas in bi-ventricular pacing, both a right side and left side lead are important for the pacing therapy. One lead, designated the first V lead is monitored 510 for performance issues. Which lead is so designated (multiple leads are often simultaneously monitored) and what those performance issues are will be explained in greater detail. However, as an example, the first V lead is the left side lead and a performance issue is a failure to capture. If during the initial pacing regimen, no performance issue is detected 510, then that pacing regimen 500 simply continues.

Alternatively, if there is a lead performance issue 510, the IMD 8 determines if there is an alternative 520 to the first V lead. In other words, is there something in place that can effectuate the same therapeutic result required of the first V lead for the initial pacing regimen? For example, a given left sided lead might have multiple electrodes. A given electrode may become unusable and fail to capture. The IMD 8, then selects and utilizes a different electrode on the same lead to deliver pacing stimulus. In this manner, the IMD 8 selects 525 the first V lead alternative and continues to deliver the initial pacing regimen 500 essentially in the same manner.

In a given situation, the IMD 8 might not include 520 any first lead alternative. Thus, the IMD 8 determines 530 the purpose of the initial pacing regimen 500. While this may be an analytical process it could also include reading an indication from memory that was set by the implanting physician or other caregiver indicative of the purpose of the initial pacing regimen or simply comparing a current pacing regimen with a look-up table of an indicated purpose. Similarly, physicians could program a prioritized list of desired pacing regimens (thus overriding the analytical or look-up table process). Alternative regimens could be selected in order, as necessary, from this prioritized list.

The IMD 8 then determines 535 if the purpose of the initial pacing regimen 500 can be effectuated by using an available lead implanted in the ventricular chamber opposite that of the first V lead (referred to herein as the second V lead). If use of the second V lead can effectuate the same purpose of the initial pacing regimen, then the IMD 8 utilizes 540 the second V lead to continue the initial pacing regimen or an appropriate variation thereof. For example, if the initial pacing regimen is bi-ventricular pacing and the first V lead (having a performance issue) is the right ventricular lead, the purpose of the regimen is resynchronization of the ventricles and this may be accomplished via the left lead alone (the second V lead in this example) by providing Fusion pacing. While this is a different pacing protocol, it does effectuate the same or similar purpose.

In some cases, the IMD 8 will not be able to effectuate the same purpose; thus, the device determines 545 what the best available secondary purpose is and effectuates that secondary purpose 550 with the second V lead. As one example, the initial pacing regimen is CRT. Assuming synchronization is no longer possible, the best secondary purpose may be to provide ventricular pacing only when intrinsic conduction fails (e.g., VPP). Often heart failure patients who benefit from CRT have good or intact intrinsic conduction. Thus, if resynchronization becomes impossible (e.g. due to loss of LV capture) then relying upon underlying conduction, with pacing capabilities in place should conduction fail, may be the most beneficial secondary purpose to the patient until the performance issue with the first V lead can be rectified.

Figure 4:
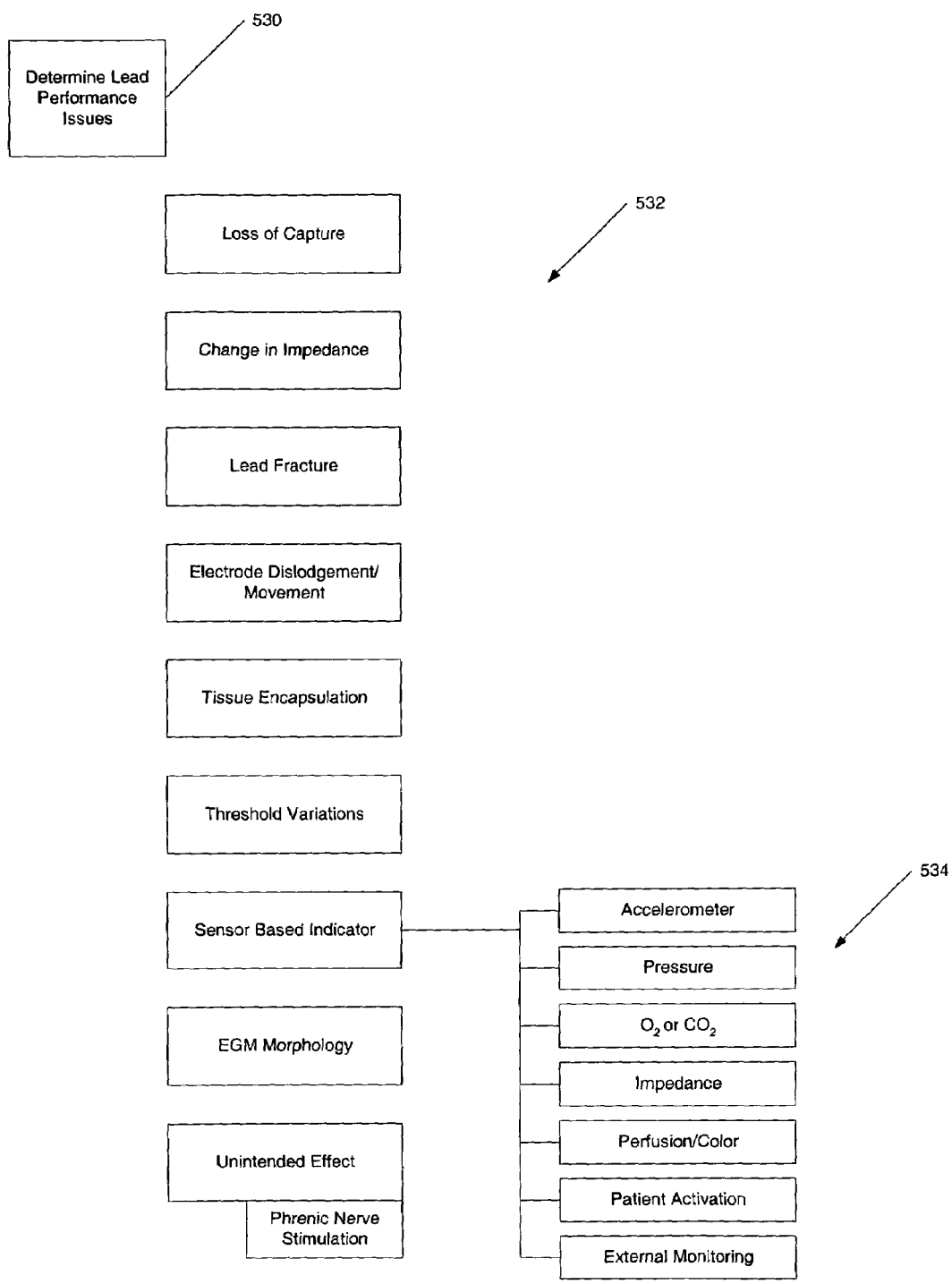
FIG. 4 is a block diagram illustrating, without limitation, examples of lead performance issues and indicators.

FIG. 4 is block diagram illustrating, without limitation, examples of lead performance issues 530 that the IMD 8 evaluates. Some examples are related and may overlap in certain cases. The exemplary issues, designated 532 include loss of capture, a change in impedance (greater than tolerances), lead fracture, electrode dislodgement or movement, tissue encapsulation, and threshold variations (greater than tolerances). The IMD 8 may include various sensor based indicators indicative of a problem (including those just mentioned and others) or confirming proper operation of various components. Such sensors 534 may include (without limitation) accelerometers, pressure sensors, $O_2$ or $CO_2$ sensors, impendence sensors, perfusion and/or color sensors, patient input, and a whole host of external sensors.

The IMD 8 can also identify potential lead performance issues by evaluating the sensed EGM (electrogram). Changes may occur due to physiological conditions but if controlled for, such variation can be indicative of a component's performance. Finally, the IMD 8 may determine an issue exists by sensing or receiving an indication of an unintended consequence. One example is phrenic nerve stimulation which may occur with a left sided lead as it is often implanted proximate this nerve. Either due to position or due to elevated levels for pacing stimulation, the phrenic nerve might be stimulated by the left sided lead and may be considered a performance issue in itself (placement issue) or indicative of another issue (e.g., what required elevated pacing stimulation levels).

In summary, there are a number of conditions or issues that may occur that are designated as a lead performance issue. Such an issue means that the lead, or at least a given electrode of that lead, cannot effectively and/or reliably provide the intended therapy within appropriate parameters and may include failures, malfunctions, dislodgment/movement but also includes variations in the patient such that the tissue or conduction pathway is non-responsive to an otherwise functioning lead/electrode. Thus, the terminology lead performance issue includes anatomical and/or physiological conditions that prevent an otherwise functional lead and/or electrode from generating an intended therapeutic result. For example, a His pacing electrode may be fully functional, but the patient may develop left bundle branch block (LBBB). This physiological condition prevents the otherwise functional lead and intact electrode from providing the intended therapy. This condition may be determined by, e.g., sensing a widened QRS complex with the His lead, another implanted lead, or any sensor utilized to sense and EGM or EKG data. Other examples of physiological changes may result in the patient altering a medication regimen. Thus, the change in medication may affect the performance of the implanted device and would therefore be a performance issue in some cases. When a performance issue is detected or determined, the IMD 8 will take the appropriate course of action as described herein. While certain examples are presented, it is to be understood that the lead performance issues and the means for determining their presence is not limited to what is described.

Figure 5:
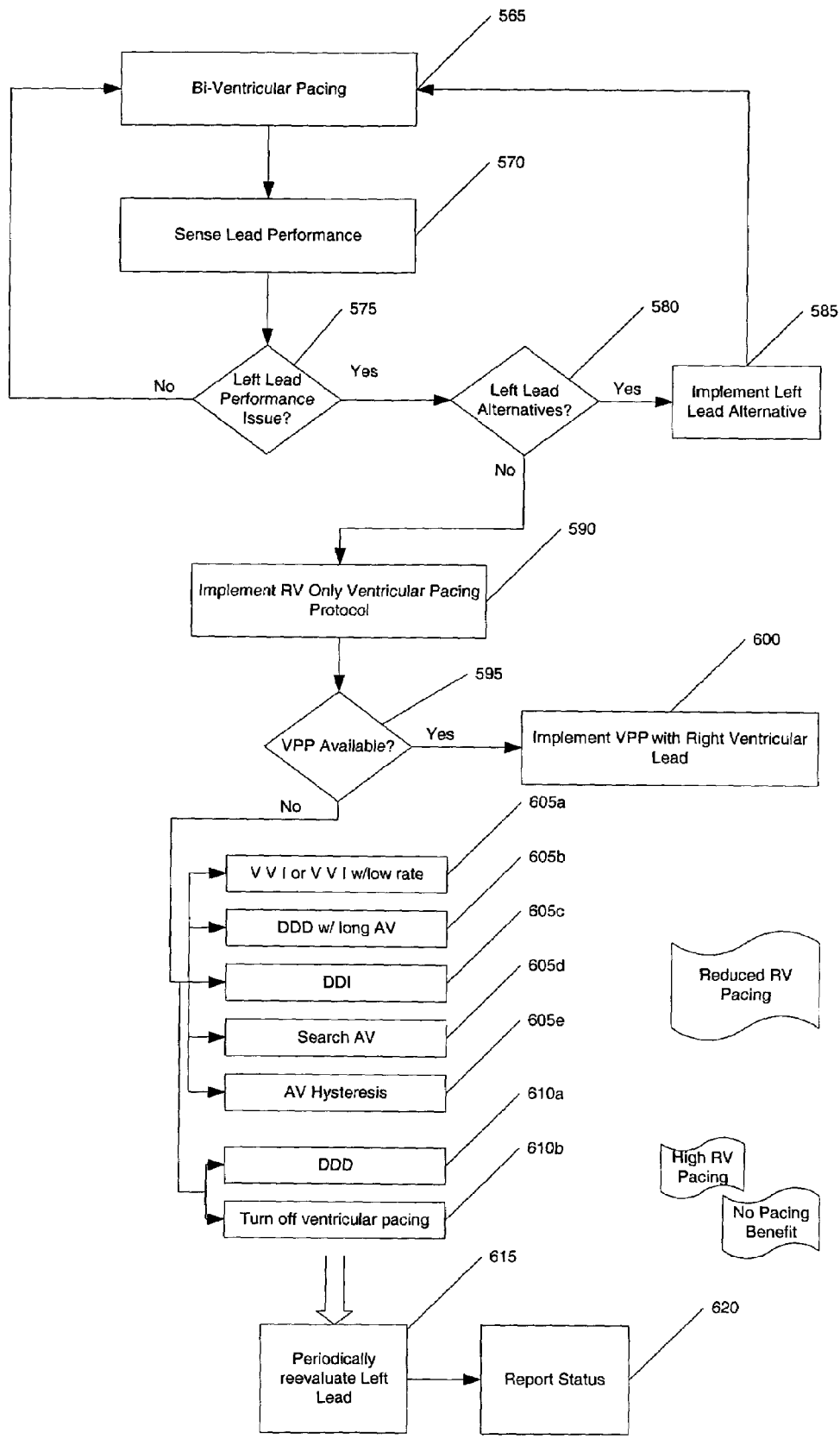
FIG. 5 is a flowchart illustrating a process for addressing left side lead performance issue during bi-ventricular pacing.

FIG. 5 is a flowchart illustrating a process for left lead performance issues when bi-ventricular pacing 565 is the initial pacing regimen 500. During the course of the therapy, pacing is provided via a right side lead and a left side lead. Right, right side or right sided are terms meant to refer to locations within, contacting or proximate the right ventricle to sense right ventricular events and/or effectuate right ventricular pacing. Left, left side and left sided are terms meant to refer to locations within, contacting, or proximate the left ventricle to sense left ventricular events and/or effectuate left ventricular pacing.

CRT via bi-ventricular pacing is a therapy that is commonly employed for patients having heart failure, though the physician may choose bi-ventricular pacing for any number of reasons. In any event, the left side lead is monitored 570 for performance issues such as a failure to capture, fracture, dislodgement, high impedance, as well as physiological or anatomical variations that prevent a functional lead or electrode from achieving the intended therapeutic effect. If there are no performance issues 575, the IMD 8 continues with the bi-ventricular pacing regimen as programmed.

If the IMD 8 determines that there is a left lead performance issue 575, the IMD 8 will then determine if there are left lead alternatives 580. Such an alternative would be another electrode on the same left lead that may be utilized, if the current electrode is the basis of the lead performance issue. Alternatively, though unlikely, a second left side lead may have been implanted and attached to the housing that may now be utilized. Yet another left side lead alternative is the use of electrodes remote from the left side (e.g., right atrium, right ventricle, can electrode) that provide a vector through the left side that permits sufficient energy to be controllably directed through the left ventricle to stimulate depolarization. In summary, the left lead alternatives 580 include any mechanism or technique to safely and reliably continue left sided ventricular pacing, absent surgical intervention. If such an alternative is available, that alternative is implemented 585 and bi-ventricular pacing continues.

The most likely left lead alternative is other electrodes on the left sided lead, if present. Even if present, such electrodes might not be properly positioned to effectuate depolarization. Furthermore, the lead performance issue may relate to a fracture or other device issue that also renders the secondary electrode ineffective or an anatomical or physiological change may be the relevant factor. In any case, the IMD 8 will identify these issues and determine whether a functional left sided lead alternative 580 is present. It should also be appreciated that the IMD 8 may selectively disable the left sided lead as opposed to a performance issue simply rendering it completely unusable or inoperable. That is, the lead performance issue may be sporadic or may involve values or settings above a desired parameter. For example, capture may be possible but only at undesirably high amplitudes.

When there is a lead performance issue 575 and no left side lead alternatives 580, then the IMD 8 is no longer able to provide left sided ventricular pacing and hence, cannot provide bi-ventricular pacing. As such, the purpose of the original pacing regimen (bi-ventricular pacing for e.g., CRT) cannot be achieved. Thus, the IMD 8 implements a right side only pacing protocol 590.

In devices having the capability, a VPP 595, such as e.g., MVP™, is implemented 600 as the right sided pacing protocol. The VPP includes the various embodiments as described in the above referenced patents and applications. As used herein, the term Ventricular Pacing Protocol (VPP) includes ventricular pacing regimens that reduce or minimize ventricular pacing. A VPP may be either a single mode or a protocol that effectuates mode switching to achieve the result. Furthermore, the VPP operates in an atrial based pacing mode or manner when intrinsic conduction is present, similar to AAI/R and has ventricular sensing capabilities. The VPP will tolerate a full cardiac cycle without ventricular activity and will assure ventricular depolarization in the subsequent cycle.

If no VPP is available 595 to the IMD 8 various other pacing protocols 605a-605e are utilized as a mechanism to attempt to limit the amount of right ventricular pacing provided until such time as the left sided ventricular lead performance issue is resolved or a decision is made that the initial pacing regimen is no longer desired. That is, the caregiver may elect not to take steps that resolve the performance issue and instead elect to utilize a different pacing regimen for any number of reasons. A standard VVI mode 605a or a standard VVI mode set to a low rate is one option. Alternatively, the IMD 8 operates in a DDD mode 605b having a long (relative to a standard DDD mode) AV delay. Thus, intrinsic depolarization is given a "longer" or greater opportunity to occur. A third alternative is to operate in a DDI mode 605c, with a longer AV interval. Fourth and fifth alternatives include utilizing a Search AV protocol 605d or AV Hysteresis protocol 605e, which attempt to provide a longer AV interval to permit intrinsic conduction to occur. Other alternatives may include a determination of the previously mentioned protocols based on rate response algorithms. That is, a DDD mode having a long AV delay may be initially chosen but when the sensor rate exceeds a certain value the new pacing protocol will be DDD with a previously defined and shortened AV delay until the sensor rate is reduced at which time the pacing protocol reverts back to DDD with a long AV delay. With each of these alternatives 605a-605e, much less than a full cardiac cycle is necessarily provided as the window during which intrinsic conduction must occur and once this window expires ventricular pacing is provided. As used herein, options 605a-605e are referred to as "DDD mode alternatives."

Two other alternatives are illustrated. The first is to implement a standard DDD pacing mode 610a. This may be selected if no VPP is available, none of the DDD mode alternatives 605a-605e are available, if preferred by the physician as a programmable setting, or finally as an evolution of the VPP 595 or one of the DDD mode alternative protocols 605a-605e. For example, if the patient loses intrinsic conduction when the VPP is in use, periodic conduction checks are made to determine if conduction returns. This may successfully occur after a single cardiac cycle, a few minutes or a few hours. At some point, the VPP could determine that long term operation in the DDD mode is appropriate as intrinsic conduction does not appear to present. Even in the DDD mode, infrequent conduction checks may still be made (e.g., once per day) but the device is essentially operating in the DDD mode.

Operation in the DDD mode, as a practical matter, generally delivers the highest frequency of right ventricular pacing; that is, most if not all cardiac cycles include a ventricular pace. This is obviously desirable in the absence of intrinsic conduction, but is less desirable if conduction exists. In summary, operation in the DDD mode 610a as an evolution of any of the previous alternatives may be necessary or appropriate. Selection of the DDD mode 610a (assuming lead placement in the right ventricular apex) as a first choice when implementing the RV only protocol 590 is certainly permissible, but generally less desirable absent patient or physician specific indications or preferences.

Alternatively, rather than implementing any right sided pacing protocol, ventricular pacing may simply be disabled 610b. The initial pacing regimen 565 was bi-ventricular pacing, a likely (though not necessarily exclusive) purpose would be ventricular resynchronization. This may very well have been prescribed as a therapy despite the patient having otherwise intact AV conduction. Thus, with the loss of use of the left lead, disabling of right ventricular pacing simply results in the patient relying upon their intact conduction and a return to unsynchronized ventricular timing. This may be preferable to providing right ventricular pacing, depending upon the given patient's condition and/or physician preferences.

As indicated in FIG. 5, the various options subsequent to step 590 may be grouped functionally. Selecting a VPP 595, will provide the least amount of right ventricular pacing and provide a greater opportunity for intrinsic conduction, if present. Naturally, if intrinsic conduction is not present, then the VPP provides pacing as necessary.

DDD mode alternatives 605a-605e, as a group, will tend to provide more ventricular pacing relative to the VPPs, but often less ventricular pacing than the DDD mode. Selecting DDD 610a will generally provide a maximum amount of ventricular pacing due to the nature of the mode. Finally, disabling pacing results in no right ventricular pacing but also fails to provide any pacing benefit even when required or beneficial.

Over time, the status of the left side lead is re-evaluated 615 to determine if the performance issue has resolved. If it has, then the process can return to delivering bi-ventricular pacing 565 and proceed accordingly. If not, then the selected alternative remains.

The lead performance issue and the action(s) taken are reported 620. In one embodiment, this occurs during a subsequent interrogation of the implantable device by a medical device programmer, either in-office or remotely. Alternatively, the IMD 8 initiates a remote telemetry session to transmit the status information to the appropriate caregiver. This may include communication with an in-home monitor provided to the patient and coupled with an appropriate communication medium, such as for example, the Medtronic CareLink Network™. This may also include direct communication to the patient via an included speaker in the IMD 8 that generates an audible signal or voice recorded message and/or a tactile alert such as a vibration generated by the IMD housing.

When evaluated by the appropriate caregiver, appropriate corrective action can be taken or scheduled. This may include replacement, repair, or repositioning of the left lead; providing an additional lead; or changing therapy (e.g., choosing not to provide bi-ventricular pacing).

Figure 6:
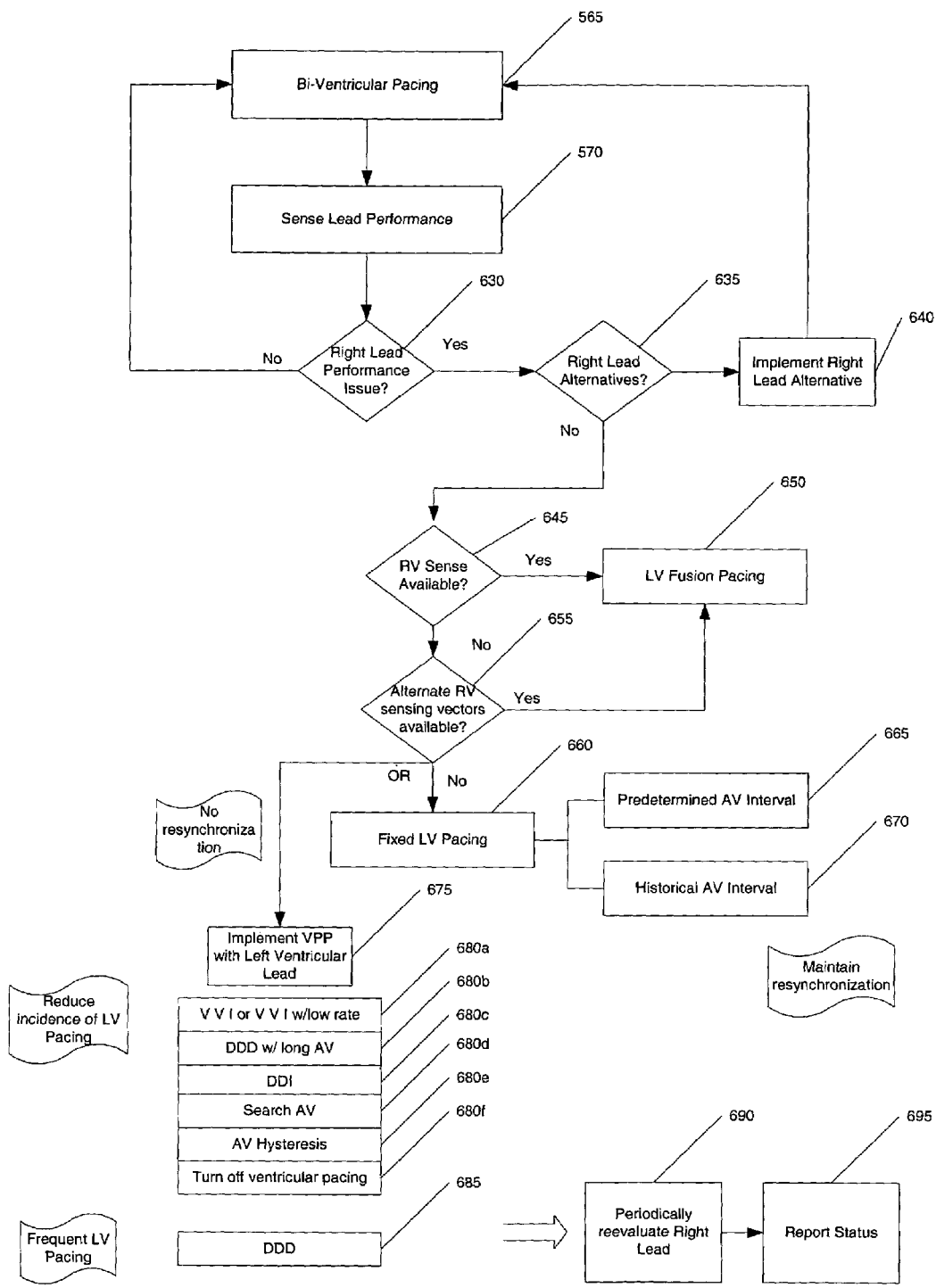
FIG. 6 is a flowchart illustrating a process for addressing right side lead performance issue during bi-ventricular pacing.

FIG. 6 illustrates a process wherein the initial pacing regimen is also bi-ventricular pacing 565 and the lead performance is sensed 570 by the IMD 8. The IMD 8 determines 630 whether there is a performance issue with the right ventricular lead, a given electrode on that lead based on a malfunction or anatomical/physiological change. If there is no performance issue, the process returns and bi-ventricular pacing 565 continues. It should be appreciated that with bi-ventricular pacing, both the left and right ventricular leads are monitored and which lead, if any, develops a performance issue determines whether the process of FIG. 5 or of FIG. 6 is selected. In other words, these processes, as described, may be cumulative and are not mutually exclusive.

If there is a right lead performance issue 630, then the IMD 8 determines if there are any right lead alternatives 635. In this instance, such an alternative means having the ability to deliver a pacing stimulus to the right ventricle that captures the tissue. As with the left lead example, this could include a second available lead for pacing the right ventricle. A more likely scenario is an alternative electrode on the right lead that may be utilized; however, as the structure and placement of the right sided lead differs from that of the left sided lead, it is less likely that an alternative electrode will be available for pacing. If a right lead alternative is available, it is implemented 640 and bi-ventricular pacing continues 565.

Assuming that no right lead alternative exists 635 for pacing, the IMD 8 determines 645 whether right ventricular sensing is available. That is, the lead performance issue may preclude the delivery of a pacing stimulus that captures the right ventricle; however, that same electrode or another electrode on the lead may still adequately sense the electrical activity within the right ventricle. Furthermore, unlike pacing where proximity to tissue is an important factor, alternative vectors 655 may be employed that provide sensing capabilities. For example, encapsulation or a malfunction of a tip electrode in the right ventricular apex may preclude pacing; yet, a ring, coil, SVC and/or can electrode may be used in various combinations for ventricular sensing.

If the lead performance issue 630 precludes right side pacing, but right ventricular sensing is available 645, 655, then the IMD 8 initiates Fusion pacing 650. As indicated, this therapy delivers a left sided pacing pulse correlated to the timing of the intrinsic right ventricular depolarization; hence, the need to have sensing capabilities for the right ventricle. In general, the intrinsic A-RV timing is sensed or determined from previous beats and the left ventricular pace is delivered prior to the RV sense. Thus, AV synchrony is maintained through rate variations, etc. With Fusion Pacing, the right and left ventricles are synchronized and the purpose of the initial pacing regimen (e.g., CRT with bi-ventricular pacing) is achieved via this alternative therapy. It should be appreciated that after being continuously paced, the right ventricle may take a period of time to return to normal intrinsic conduction. As such, the timing and implementation of Fusion pacing 650 should account for this factor.

If the lead performance issue 630 and/or the configuration of the device preclude right ventricular sensing 645, 655, then the IMD 8 may take one of two options. The first option is to provide LV only pacing 660 based on a fixed AV (A-LV) interval, referred to as "blind" LV pacing. The fixed AV interval may be a predetermined 665 or pre-programmed value as set by the caregiver. This may be a static value or may vary depending upon another parameter such as heart rate. In other words, for each rate or rate range a predetermined A-LV interval value is programmed. Fusion pacing, as used herein generally means that the LV pace is delivered based upon the timing of intrinsic conduction to the right ventricle (sensed directly or indirectly via another type of sensor). This allows the LV pacing to be adaptive to the intrinsic conduction. Absent the ability to sense intrinsic conduction, the LV pacing is no longer adaptive thereto; however, pacing is provided.

Alternatively, the IMD 8 may determine 670 an appropriate AV interval. This determination would be based on historical timing patterns that occurred prior to the right lead performance issue. Various algorithms may be employed to provide this data. For example, the A-LV interval may be averaged over time and this averaged value is utilized. More complex algorithms may include averaged values for given events, such as heart rate. Thus, for a given heart rate or rate range a corresponding A-LV value is determined and recorded.

Utilizing a "fixed" AV value 660 therefore means that the left sided pace is not timed from a sensed right ventricular event. As noted, with Fusion pacing, RV sensing allows the timing to be determined and the LV pace is delivered prior to a corresponding RV event. Even in this context, however, there may be variability from beat to beat in the A-LV value based on other parameters such as rate. As indicated, this option will generally maintain at least some degree of resynchronization.

The second option available when no right ventricular sensing is available is to forego attempts at ventricular resynchronization. Thus, left sided pacing is provided as a means to depolarize both ventricles and the AV timing is set accordingly. To the extent that resynchronization will be foregone, then the preference to rely upon the patient's intrinsic conduction becomes the secondary purpose, if appropriate. Thus, the VPP, such as e.g., MVP™, is utilized 675 on the left side if the IMD 8 has such a capability. Without having a VPP, the IMD 8 may utilize the various other DDD alternative modes to attempt to reduce the number of ventricular pacing pulses. The IMD 8 may utilize VVI or VVI with a lower rate 680a (lower with respect to a previous rate for a given activity level). Other options include using a DDD mode with a longer AV delay (as compared to standard DDD) 680b; DDI/R 680c, Search AV 680d, or AV Hysteresis 680e. Ventricular pacing may be disabled 680f in its entirety, as an option with the same caveats discussed above.

In summary, without RV sensing, LV only pacing may be provided. In the first option 660, the timing is selected to attempt to produce a resynchronization effect based upon fixed values 665 or historical data 670 to arrive at a calculated response. This is a "blind" attempt to achieve results similar to Fusion pacing. To achieve this effect, intrinsic conduction through the right ventricle still must occur, even though no longer sensed. In the second option 675, the LV pacing timing is not selected to attempt to produce a resynchronization effect but only to effectuate ventricular depolarization.

A DDD mode may be employed 685 with the left side lead. Once again, this will result in the highest frequency of delivered pacing pulses. This may be the appropriate evolution of one of the above protocols if intrinsic conduction fails, would be appropriate in the known absence of intrinsic conduction, or is selected based upon patient parameters or caregiver preferences.

Similar to the process with respect to a left lead failure, the IMD 8 will periodically re-evaluate the right side lead to determine 690 if the lead performance issue is still an impediment. Finally, the data is reported 695, as previously indicated.

FIG. 7 is a flowchart illustrating a process for addressing a lead performance issue when left ventricular Fusion pacing 700 is the initial pacing regimen 500. The left lead is sensed 705 and the IMD 8 determines if there is a performance issue 710. If not, then Fusion pacing 700 continues. If a performance issue exists, then the IMD 8 determines 715 if there are any left lead (or given electrode) alternatives. If there are, the alternative lead (or electrode) is implemented 720 and any modification to the A-LV (or V-V) timing required due to the alternative lead position is made 725. Then using the alternative left sided lead or electrode, Fusion pacing 700 continues. As indicated, the terminology left lead alternative is meant to include additional left side leads already present and/or alternative electrodes or electrode configurations on the lead itself.

At step 715, the IMD 8 may determine that there are no left lead alternatives. As Fusion pacing is based upon the timing sensed in the right ventricle, there is a high likelihood that a right ventricular pacing lead is implanted. Assuming that there is, steps 590-620 are substantially the same as described with respect to FIG. 5.

It is possible that a given IMD 8 implanted for Fusion pacing might not include a right sided lead or may include a right sided lead that only has sensing capabilities. In such a scenario, no ventricular pacing (610b) is possible until the performance issue is resolved. Again, for patients receiving pacing for resynchronization, there is a high likelihood that their intrinsic conduction is intact and ventricular depolarizations occur, even if less than hemodynamically ideal.

Figure 8:
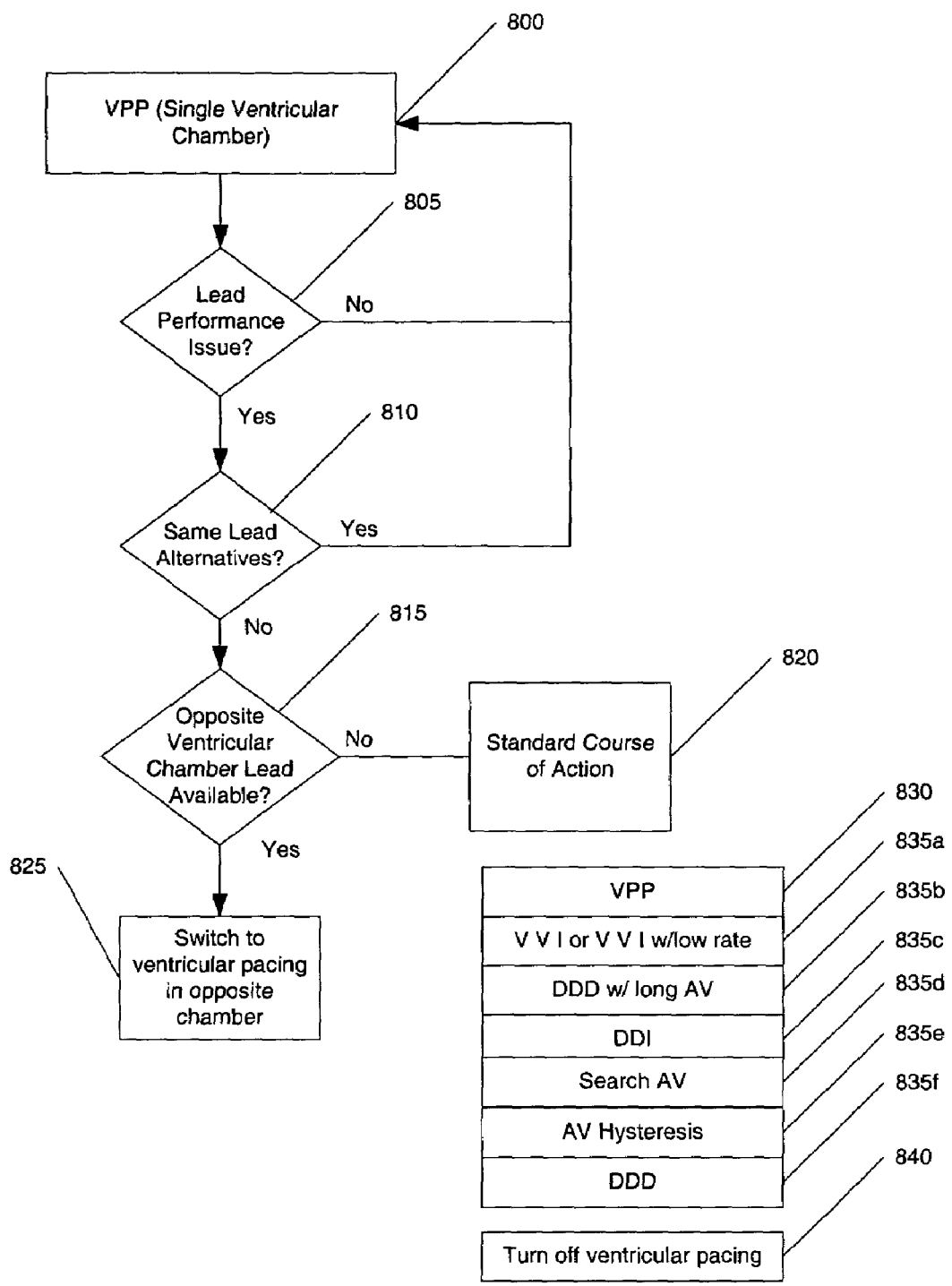
FIG. 8 is a flowchart illustrating a process for addressing a ventricular lead performance issue while using a VPP.

FIG. 8 illustrates a process for addressing lead performance issues when a VPP 800, such as e.g., MVP™ is the initial pacing regimen. In this instance, the process is the same regardless of whether the initial VPP pacing lead is on the left or the right side. The IMD 8 will sense the performance 805 of the ventricular lead and in the absence of any performance issue, continue with the VPP.

If the IMD 8 identifies a lead performance issue 805, a determination 810 is made as to whether any alternative lead or electrodes are available on the same side. If so, that alternative lead or electrode is employed and the VPP continues. If no alternative exists in the same ventricular chamber 810, then the IMD 8 determines 815 if there is a ventricular pacing lead in the opposite ventricular chamber. If not, then the IMD 8 initiates 820 a standard course of action when such a performance issue occurs. That may include, without limitation, alerting the patient or alerting the caregiver.

Assuming a pacing lead is present in the opposite ventricular chamber, IMD 8 then switches 825 to ventricular pacing utilizing that pacing lead. Presumably, the IMD 8 would employ the same VPP on the opposite side as was utilized in the initial ventricular chamber. Based upon patient parameters or caregiver preferences, modes and protocols 835a-835f (DDD mode alternatives and DDD mode) may be employed with the lead in the opposite ventricular chamber. As always, the option to disable 840 ventricular pacing also exists. As previously described, the VPP serves to reduce or minimize the number of ventricular pacing pulses. The use of VVI or VVI with a low rate 835a; DDD with a long AV delay 835b, DDI 835c, Search AV 835d, or AV Hysteresis 835e will often lower the frequency of ventricular pacing as compared to the use of DDD mode 835f. Disabling ventricular pacing 840 obviously has the lowest frequency of pacing that is zero; however, no ventricular pacing benefit is provided or available even when required or beneficial. Though not separately illustrated, the actions taken are reported as appropriate.

Figure 9:
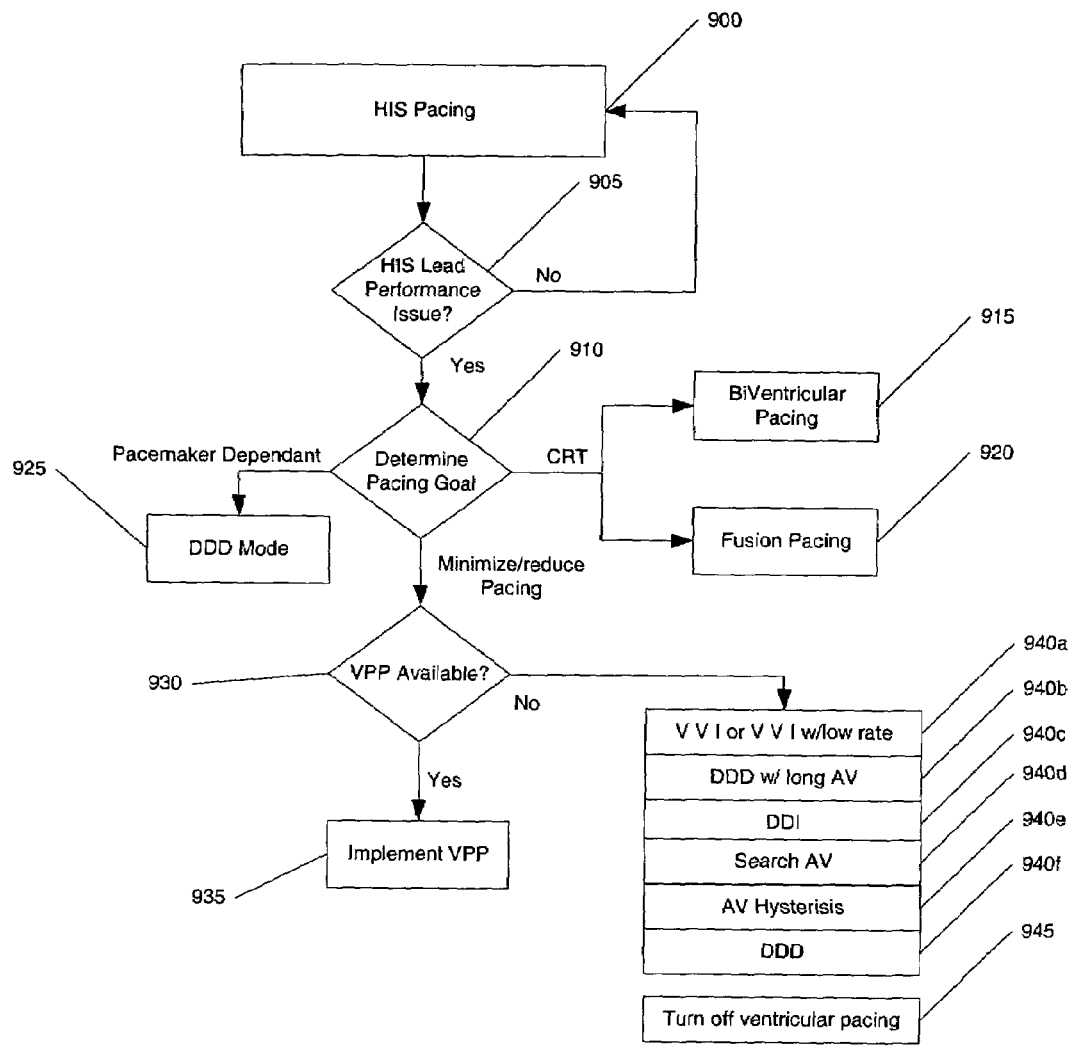
FIG. 9 is a flowchart illustrating a process for addressing a His Bundle lead performance issue during His Bundle pacing.

FIG. 9 is a flowchart illustrating a process for addressing lead performance issues if HIS pacing or HIS Bundle pacing 900 is the initial pacing regimen. The IMD 8 determines 905 if there is a performance issue with the HIS pacing lead; assuming there is no performance issue then HIS pacing continues.

If there is a performance issue, then the IMD 8 determines 910 what the appropriate goal of an alternative pacing regimen is based upon either patient parameters or preprogrammed indications. HIS pacing requires a rather precise lead placement and it would be unlikely that any HIS pacing lead alternatives would exist; of course, to the extent that such an alternative is in place it would be utilized to continue HIS pacing but such an option is not illustrated in the flowchart. The same types of lead performance issues previously discussed are relevant here; in addition, the precise placement of the lead relative to the HIS Bundle that is required and the potential to alter the anatomical conduction pathway due to lead placement and/or pacing stimulation are prevalent potential issues. In other words, these factors could inhibit or prevent successful pacing even with a completely functional lead. Other physiological conduction path issues, such as e.g., LBBB may develop, likewise preventing efficacious therapy delivery, despite a fully operational and properly placed lead.

As indicated, the IMD 8 determines which pacing goal should be employed. One option is to provide CRT via bi-ventricular pacing 915 or Fusion pacing 920 (including the Fusion pacing alternatives described above). If HIS pacing was the only ventricular pacing provided prior to the performance issue, then the patient's conduction pathway subsequent to the HIS Bundle is presumably intact. Thus, CRT is not a likely alternative in this instance. There are however several instances where CRT would be the appropriate alternative. In one example, the patient's condition has changed such that CRT becomes a preferable therapy. Alternatively, where ventricular pacing is required (e.g., complete block), pacing both the left and right side may be preferential to only pacing the right side (via the right ventricular apex) even absent a traditional need (e.g., heart failure) for resynchronization. Of course, the original configuration may have included a HIS pacing lead and, due to an interruption in the conduction pathway specific to one ventricle, a ventricular pacing lead. In other words, CRT was being delivered by utilizing the HIS pacing lead for one specific chamber; thus, CRT will continue with an alternative arrangement. These examples are non-limiting and other circumstances may warrant providing CRT if a lead performance issue occurs with a HIS pacing lead.

The IMD 8 may determine 910 that the patient is pacemaker dependant (e.g., complete heart block) and utilize 925 a conventional DDD mode with an available right or left ventricular lead. If the patient has intact AV conduction, then the IMD 8 determines if a VPP is available 930 and if so, selects the VPP. If no VPP is available, then the IMD 8 selects a DDD alternative mode or protocol 940a-940e that will preferably at least partially reduce the number of ventricular pacing pulses as compared to e.g., a DDD mode. Of course, with any of these options 940a-940e as well as with the VPP, the patient's conduction may deteriorate and selection of a DDD mode 940f becomes appropriate. As always, the selection of alternatives, including immediate selection of the DDD mode may be a preference programmed by the caregiver. Finally, the option to disable 945 ventricular pacing exists, with the advantages and risks previously discussed.

Again, though not separately illustrated such events and actions are appropriately reported from the IMD 8.

Figure 10:
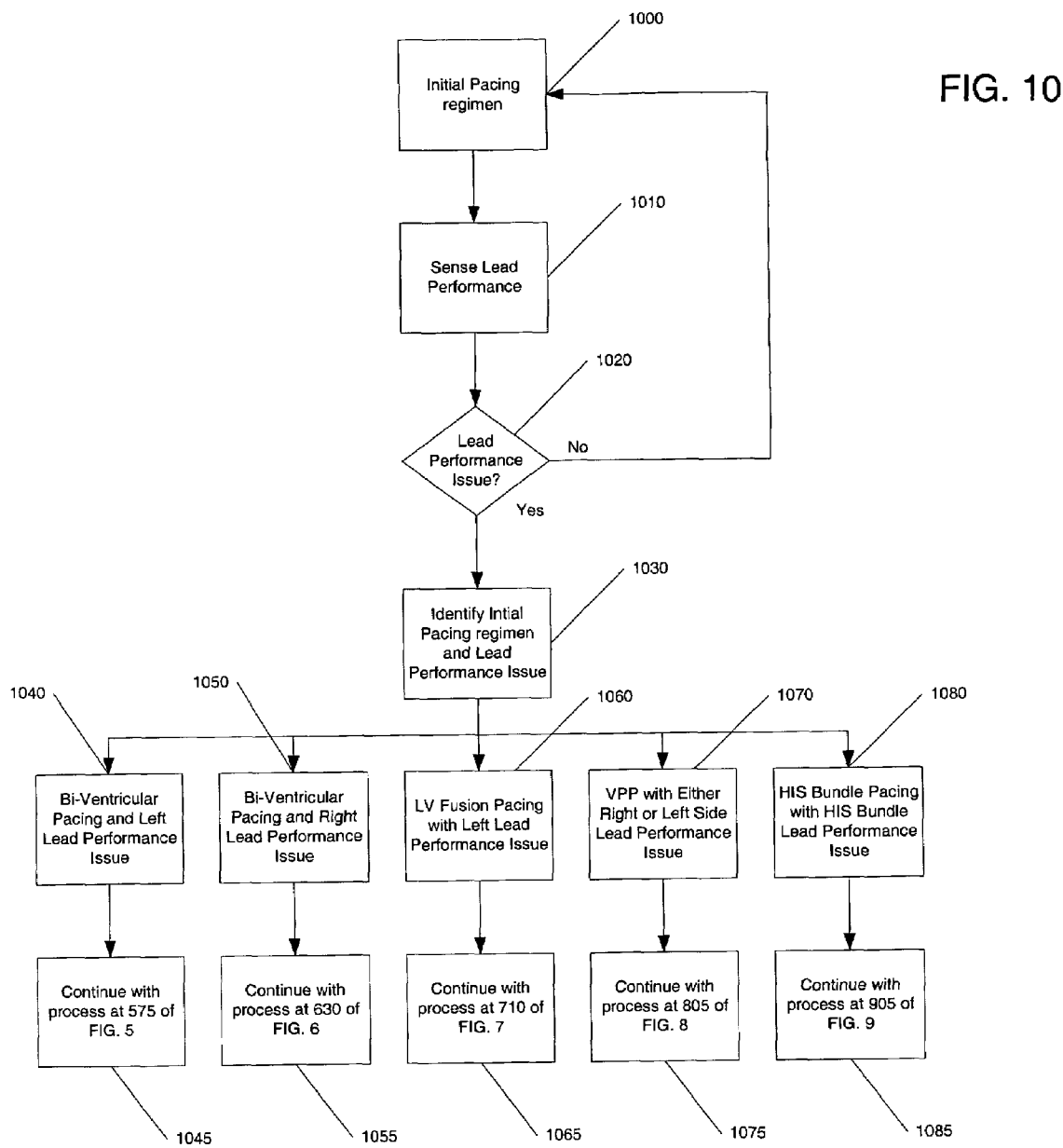
FIG. 10 is a flowchart illustrating a process for determining a pacing regimen and an appropriate course of action if a lead performance issue occurs.

FIG. 10 is a flowchart illustrating a process employed by the IMD 8 to identify and address lead performance issues. The initial pacing regimen 1000 is employed and the lead performance is sensed 1010. Assuming that no lead performance issue exists 1020, the initial pacing regimen continues.

If a lead performance issue is identified 1020, the IMD 8 identifies 1030 what the initial pacing regimen is and which lead is having a performance issue. If the initial pacing regimen is bi-ventricular pacing and there is a left lead performance issue 1040, then the IMD 8 continues 1045 with the process as described from 575 of FIG. 5. If there was a right lead performance issue 1050 with the initial pacing regimen of bi-ventricular pacing, then the IMD continues 1055 with the process as described from 630 of FIG. 6.

When Fusion pacing 1060 is the initial pacing regimen and left sided lead has a performance issue, the IMD 8 continues 1065 with the process as described from 710 of FIG. 7. Should a performance issue occur 1070 with either a right side or left side lead when a VPP is the initial pacing regimen, the IMD 8 will continue 1075 with the process from 805 of FIG. 8. If a HIS Bundle Pacing lead has a performance issue 1080, the IMD continues 1085 with the process from 905 of FIG. 9.

As described, a given patient will have an IMD 8 configured to provide a particular therapy based upon the patient's particular circumstances and their caregivers medical decisions and preferences. Subsequently, a lead used for that therapy may have a performance issue such as a malfunction with the lead and/or an anatomical or physiological change within the patient that prevents the delivered therapy from being efficacious. The present invention provides a process to identify the performance issue, select, and provide either an alternative mechanism for providing the same or similar therapy or for selecting an alternative therapy.

The invention claimed is:

1. A method comprising:
    employing a cardiac pacemaker having atrial and right and left ventricular electrode bearing leads to deliver a first pacing regimen for a first therapy, wherein the first pacing regimen includes a cardiac resynchronization therapy, wherein the cardiac resynchronization therapy comprises delivering atrial pacing pulses and delivering pacing pulses to the left ventricle synchronized to the delivered atrial pacing pulses;
    determining if a performance issue exists for the left ventricular lead;
    discontinuing the first pacing regimen if the performance issue is determined to exist and thereafter delivering a second pacing regimen using the right ventricular lead according to a Ventricular Pacing Protocol (VPP), wherein the VPP tolerates a complete cardiac cycle between delivered atrial pacing pulses devoid of ventricular activity while providing for ventricular pacing in the cycle immediately subsequent to the cardiac cycle devoid of ventricular activity.

2. The method of claim 1, wherein determining if a performance issue exists comprises determining if a left ventricular lead alternative exists.

3. The method of claim 2, wherein determining if a left ventricular lead alternative exists includes identifying alternative available electrodes on the left ventricular lead.

4. The method of claim 1, wherein the first pacing regimen is bi-ventricular pacing.

5. The method of claim 1, wherein the first pacing regimen is Fusion pacing.

6. An implantable cardiac pacemaker having atrial and right and left ventricular leads, comprising:
    means for implementing a first pacing regimen for a first therapy wherein the first pacing regimen includes cardiac resynchronization therapy, wherein the cardiac resynchronization therapy comprises delivering atrial pacing pulses and delivering pacing pulses to the left ventricle synchronized to the delivered atrial pacing pulses;
    means for determining if a performance issue exists for the left ventricular lead;
    means for discontinuing the first pacing regimen if the performance issue is determined to exist and for thereafter implementing a second pacing regimen using the right ventricular lead according to a Ventricular Pacing Protocol (VPP), wherein the VPP tolerates a complete cardiac cycle between atrial pacing pulses devoid of ventricular activity while providing for ventricular pacing in the cycle immediately subsequent to the cardiac cycle devoid of ventricular activity.

7. The pacemaker of claim 6,
    wherein the means for determining if a performance issue exists further comprises means for determining if a left ventricular lead alternative exists.

8. The pacemaker of claim 6, wherein the first pacing regimen is bi-ventricular pacing.

9. The pacemaker of claim 6, wherein the first pacing regimen is Fusion pacing.

10. A method comprising:
    employing a cardiac pacemaker having atrial and first and second ventricular electrode bearing leads to deliver a first pacing regimen for a first therapy, wherein the first pacing regimen includes a cardiac resynchronization therapy, wherein the cardiac resynchronization therapy comprises delivering atrial pacing pulses and delivering ventricular pacing pulses using a said ventricular lead, synchronized to the delivered atrial pacing pulses;
    determining if a performance issue exists for a said ventricular lead employed to deliver the first therapy;
    discontinuing the first pacing regimen if the performance issue is determined to exist and thereafter delivering a second pacing regimen using another of the said ventricular leads according to a Ventricular Pacing Protocol (VPP), wherein the VPP tolerates a complete cardiac cycle between delivered atrial pacing pulses devoid of ventricular activity while providing for ventricular pacing in the cycle immediately subsequent to the cardiac cycle devoid of ventricular activity.

11. The method of claim 10,
    wherein determining if a performance issue exists further comprises determining if a lead alternative exists for delivering the first therapy.

12. The method of claim 11, wherein determining if a lead alternative exists includes identifying alternative available electrodes on the said lead determined to have the performance issue.

13. The method of claim 10, wherein the first pacing regimen is bi-ventricular pacing.

14. The method of claim 10, wherein the first pacing regimen is Fusion pacing.

15. An implantable cardiac pacemaker having atrial and first and second ventricular electrode bearing leads, comprising:
    means for implementing a first pacing regimen for a first therapy, wherein the first pacing regimen includes cardiac resynchronization therapy, wherein the cardiac resynchronization therapy comprises delivering atrial pacing pulses and delivering ventricular pacing pulses using a said ventricular lead, synchronized to the delivered atrial pacing;

means for determining if a performance issue exists for a said ventricular lead used to deliver the first therapy;

means for discontinuing the first pacing regimen if the performance issue exists and for thereafter implementing a second pacing regimen using another of the said ventricular leads according to a Ventricular Pacing Protocol (VPP), wherein the VPP tolerates a complete cardiac cycle between atrial pacing pulses devoid of ventricular activity while providing for ventricular pacing in the cycle immediately subsequent to the cardiac cycle devoid of ventricular activity.

16. The pacemaker of claim 15,
wherein the means for determining if a performance issue exists further comprises means for determining if a lead alternative exists.

17. The pacemaker of claim 16, wherein the means for determining if a lead alternative exists comprises means for identifying alternative available electrodes on the lead determined to have the performance issue.

18. The pacemaker of claim 15, wherein the first pacing regimen is bi-ventricular pacing.

19. The pacemaker of claim 15, wherein the first pacing regimen is fusion pacing.

* * * * *